US012599287B2

(12) United States Patent (10) Patent No.: US 12,599,287 B2
Mo et al. (45) Date of Patent: Apr. 14, 2026

(54) SELF-LOCKING DEVICE OF ENDOSCOPE

(71) Applicant: HUNAN VATHIN MEDICAL INSTRUMENT CO., LTD., Xiangtan (CN)

(72) Inventors: Wenjun Mo, Xiangtan (CN); Peng Tang, Xiangtan (CN); Guanhua Zhou, Xiangtan (CN)

(73) Assignee: HUNAN VATHIN MEDICAL INSTRUMENT CO., LTD., Xiangtan (CN)

( * ) Notice: Subject to any disclaimer, the term of this patent is extended or adjusted under 35 U.S.C. 154(b) by 1050 days.

(21) Appl. No.: 17/765,449

(22) PCT Filed: Dec. 30, 2020

(86) PCT No.: PCT/CN2020/141409
§ 371 (c)(1),
(2) Date: Mar. 31, 2022

(87) PCT Pub. No.: WO2021/179760
PCT Pub. Date: Sep. 16, 2021

(65) Prior Publication Data
US 2022/0409019 A1 Dec. 29, 2022

(30) Foreign Application Priority Data

Mar. 12, 2020 (CN) .......................... 202010170931.1

(51) Int. Cl.
*A61B 1/00* (2006.01)
*A61B 1/005* (2006.01)

(52) U.S. Cl.
CPC ...... *A61B 1/00066* (2013.01); *A61B 1/00042* (2022.02); *A61B 1/0052* (2013.01)

(58) Field of Classification Search
CPC ............ A61B 1/00066; A61B 1/00042; A61B 1/0052
See application file for complete search history.

(56) References Cited

U.S. PATENT DOCUMENTS

2011/0088498 A1 4/2011 Ettwein et al.

FOREIGN PATENT DOCUMENTS

CN 102813498 A 12/2012
CN 103654693 A 3/2014
CN 206007206 U * 3/2017
(Continued)

*Primary Examiner* — Michael J Carey
*Assistant Examiner* — Christen A. Sharpless
(74) *Attorney, Agent, or Firm* — Bayramoglu Law Offices LLC

(57) ABSTRACT
A self-locking device of an endoscope includes a connecting assembly and a fitting assembly. The connecting assembly includes a driven gear and a toggle lever, and the driven gear and the toggle lever are fitted with each other through pins. The fitting assembly includes a driving gear, and the driving gear is engaged with the driven gear through the toggle lever. The self-locking device realizes self-locking with a desired effect through the engagement of the driven gear and the driving gear. Through the design of a lever structure, the self-locking device switches the driven gear and the driving gear between engaged and disengaged states without resorting to an external force of a part, which avoids the use of the part and extends the service life of the device.

14 Claims, 5 Drawing Sheets

(56)          References Cited

FOREIGN PATENT DOCUMENTS

| | | | |
|----|-----------|---|---------|
| CN | 107088044 | A | 8/2017  |
| CN | 110432853 | A | 11/2019 |
| CN | 110575115 | A | 12/2019 |
| CN | 111202488 | A | 5/2020  |
| CN | 111803008 | A | 10/2020 |
| CN | 111803009 | A | 10/2020 |
| CN | 111803010 | A | 10/2020 |
| CN | 212140390 | U | 12/2020 |

* cited by examiner

SELF-LOCKING DEVICE OF ENDOSCOPE

CROSS REFERENCE TO THE RELATED APPLICATIONS

This application is the national phase entry of International Application No. PCT/CN2020/141409, filed on Dec. 30, 2020, which is based upon and claims priority to Chinese Patent Application No. 202010170931.1, filed on Mar. 12, 2020, the entire contents of which are incorporated herein by reference.

TECHNICAL FIELD

The present invention relates to the technical field of medical devices, and more particularly, to a self-locking device of an endoscope.

BACKGROUND

At present, endoscopes are widely used in the medical field. In experiments or operations, medical workers control the position of the lens of the endoscope in the human body through the toggle handle, and they often cannot let go of their hands that operate the toggle handle while observing the internal structure of the human body.

Currently, the endoscopes on the market have the following disadvantages:

(1) The endoscope cannot be self-locked, and the operator needs to keep pressing the toggle handle, which is inconvenient.

(2) The self-locking part (e.g. brake type) is easily worn or damaged, resulting in low usage for the device.

SUMMARY

The purpose of this part is to outline some aspects of the embodiments of the present invention and to briefly describe some preferred embodiments. Some simplification or omission may be made in this part as well as in the abstract of specification and the title of the disclosure of the present application to avoid blurring the purposes of this part, the abstract of specification and the title of the disclosure, and such simplification or omission cannot be used to limit the scope of the present invention.

The present invention is provided in view of the problems as mentioned above and/or existing in the prior art.

An objective of the present invention is to provide a self-locking device of an endoscope.

To solve the above technical problem, the present invention adopts the following technical solution. A self-locking device of an endoscope includes: a connecting assembly, including a driven gear and a toggle lever, where the driven gear and the toggle lever are fitted with each other through pins; and a fitting assembly, including a driving gear, where the driving gear is engaged with the driven gear through the toggle lever.

In a preferred solution of the self-locking device of an endoscope of the present invention, the toggle lever may include a gear connecting block and a toggle piece, and the gear connecting block and the toggle piece may be integrally formed; and the gear connecting block may be provided with a semi-annular cross section, and an internal angle between the gear connecting block and the toggle piece may be 45-90°.

In a preferred solution of the self-locking device of an endoscope of the present invention, the driven gear may include connecting protrusions, and the connecting protrusions may be respectively provided with limiting holes; the gear connecting block may be provided with clamping protrusions, the clamping protrusions may be respectively provided with connecting holes, and the connecting holes may be fitted with the limiting holes through the pins; and the limiting holes may be provided with a notch-shaped cross section, and have a diameter identical to a diameter of the connecting holes and a length greater than the diameter.

In a preferred solution of the self-locking device of an endoscope of the present invention, the self-locking device may further include a fixing assembly; the fixing assembly may include a central shaft and a positioning member; the positioning member may be fixed to the central shaft by a bolt; the driving gear and the driven gear may be sequentially sleeved on the central shaft; and the toggle piece may be connected to the positioning member through a pin shaft.

In a preferred solution of the self-locking device of an endoscope of the present invention, the fitting assembly may further include a gear fixing member; the gear fixing member may be fixed to the central shaft, and the gear fixing member may include a central protruding block and a rubber ring; the rubber ring may be sleeved on an outer contour of the central protruding block; and the driving gear may be sleeved on an outer side of the rubber ring.

In a preferred solution of the self-locking device of an endoscope of the present invention, the connecting assembly may further include a toggle handle, and one end of the toggle handle may be hinged to the toggle piece.

In a preferred solution of the self-locking device of an endoscope of the present invention, the connecting assembly may further include an elastic piece, and the elastic piece may be attached to the driven gear; the elastic piece may be provided with first protrusions; and the first protrusions may be fitted with surfaces of the clamping protrusions of the gear connecting block that abut against the elastic piece.

In a preferred solution of the self-locking device of an endoscope of the present invention, the elastic piece may further include second protrusions, and the second protrusions may be respectively co-linear with the first protrusions.

In a preferred solution of the self-locking device of an endoscope of the present invention, the fixing assembly may further include a handle limiting member, and the handle limiting member may be fixed to the other side of the central shaft.

In a preferred solution of the self-locking device of an endoscope of the present invention, the fixing assembly may further include a connecting shaft, and the connecting shaft may pass through the toggle handle, and may be connected to the handle limiting member.

The present invention has the following beneficial effects:

(1) The self-locking device realizes self-locking with a desired effect through the engagement of the driven gear and the driving gear.

(2) Through the design of a lever structure, the self-locking device switches the driven gear and the driving gear between engaged and disengaged states without resorting to an external force of a part, which avoids the use of the part and extends the service life of the device.

BRIEF DESCRIPTION OF THE DRAWINGS

To describe the technical solutions in the embodiments of the present invention more clearly, the following briefly describes the drawings required for describing the embodiments or the prior art. Apparently, the drawings in the following description show merely some of the embodiments of the present invention, and those of ordinary skill in the art may still derive other drawings from these drawings without creative efforts. Drawings.

Figure 1:
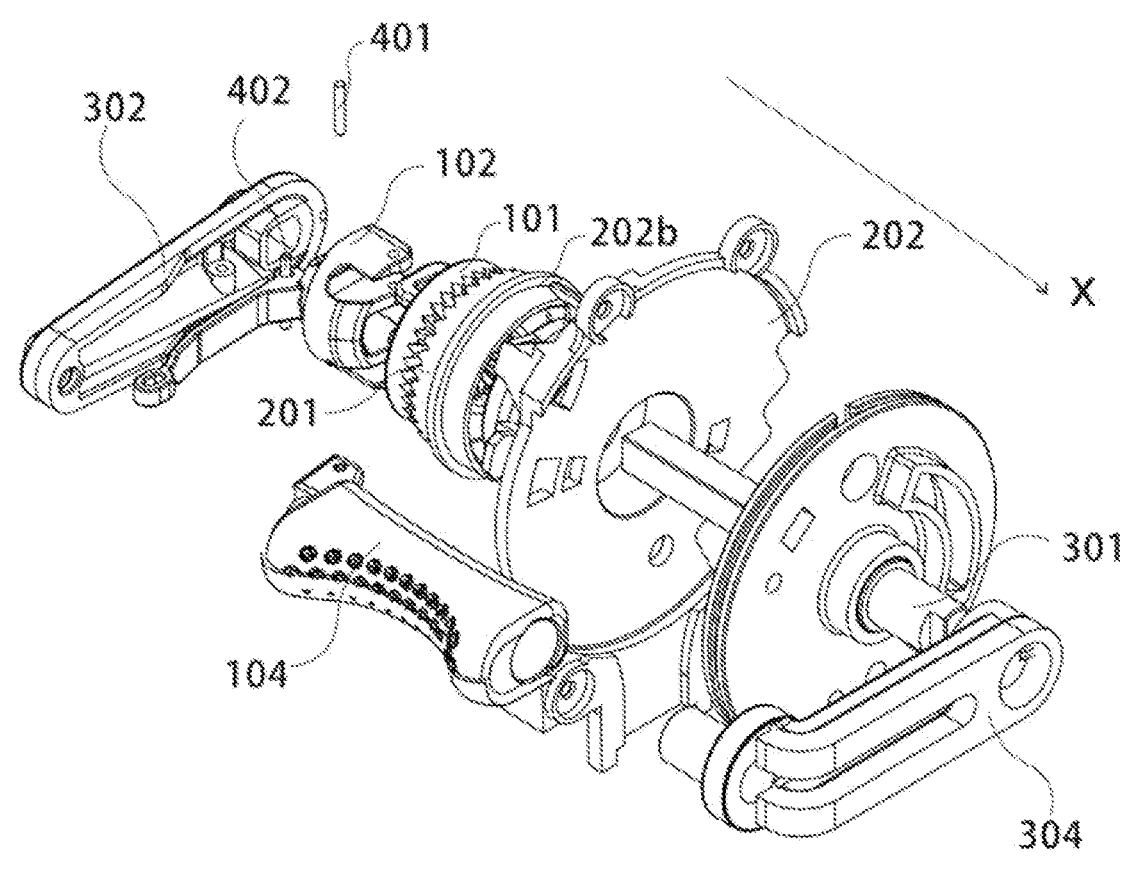
FIG. 1 is a partial exploded view of a self-locking device of an endoscope from an angle according to the present invention.

REFERENCE NUMERALS 100. connecting assembly; 101. driven gear; 101*a*. connecting protrusion; 101*a*-1. limiting hole; 102. toggle lever; 102*a*. gear connecting block; 102*a*-1. clamping protrusion; 102*a*-2. connecting hole; 102*a*-3. pressing protrusion; 102*b*. toggle piece; 103. elastic piece; 103*a*. first protrusion; 103*b*. second protrusion; and 104. toggle handle;

200. fitting assembly; 201. driving gear; 201*a*. locking protrusion; 202. gear fixing member; 202*a*. central protruding block; 202*b*. rubber ring; and 202*c*. limiting post;

300. fixing assembly; 301. central shaft; 302. positioning member; 304. handle limiting member; 305. connecting shaft;

401. pin; and 402. pin shaft.

DETAILED DESCRIPTION OF THE EMBODIMENTS

To make the above objectives, features and advantages of the present invention clearer, the specific implementations of the present invention are described in detail below with reference to the drawings of the specification.

Many specific details are set forth in the following description to facilitate full understanding of the present invention, but the present invention may also be implemented in other ways different from those described herein, similar derivatives may be made by those skilled in the art without departing from the connotation of the present invention, and therefore, the present invention is not limited by the specific embodiments disclosed below.

In addition, the "one embodiment" or "embodiments" herein refers to a particular feature, structure or characteristic that may be included in at least one implementation of the present invention. The "in an embodiment" appearing in different places in the specification does not refer to the same embodiment or an individual or alternative embodiment mutually exclusive with other embodiment.

Embodiment 1

Figure 2:
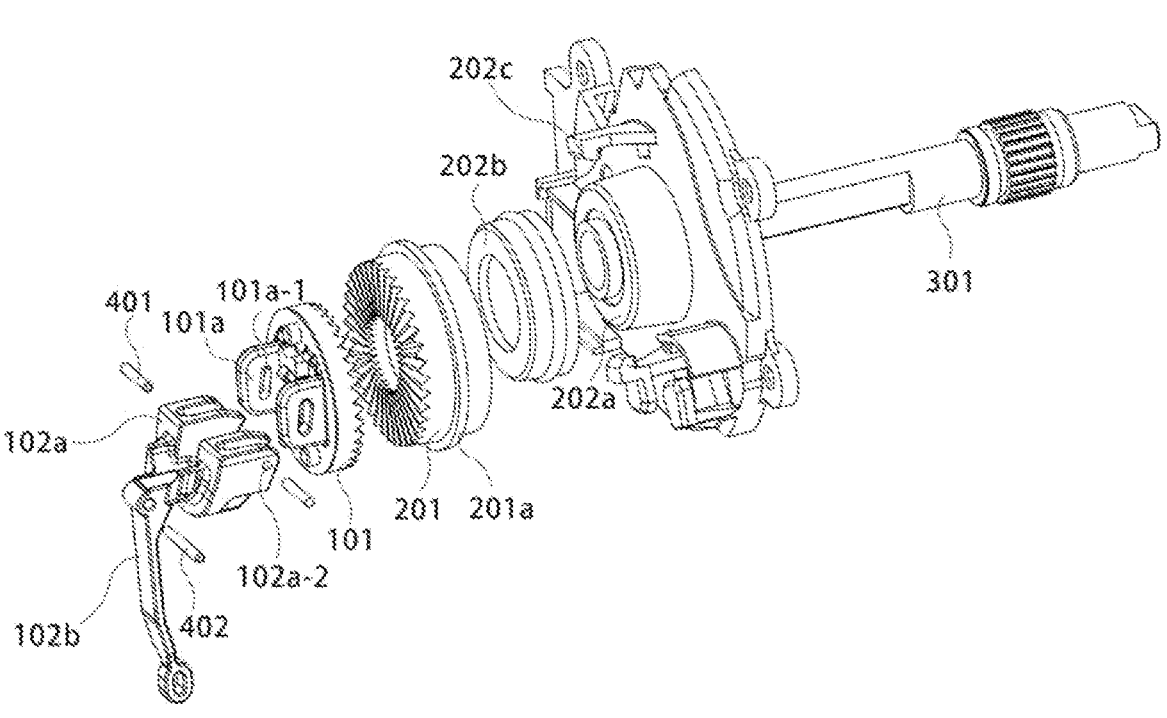
FIG. 2 is a partial exploded view of the self-locking device of an endoscope from another angle according to the present invention.
Figure 3:
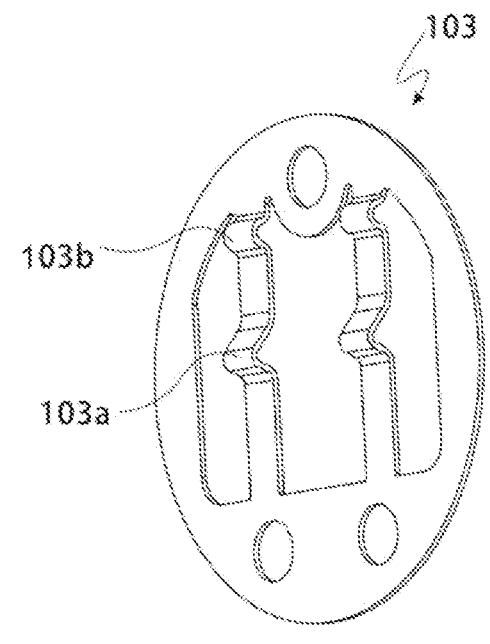
FIG. 3 is a full structural view of an elastic piece of the self-locking device of an endoscope according to the present invention.
Figure 4:
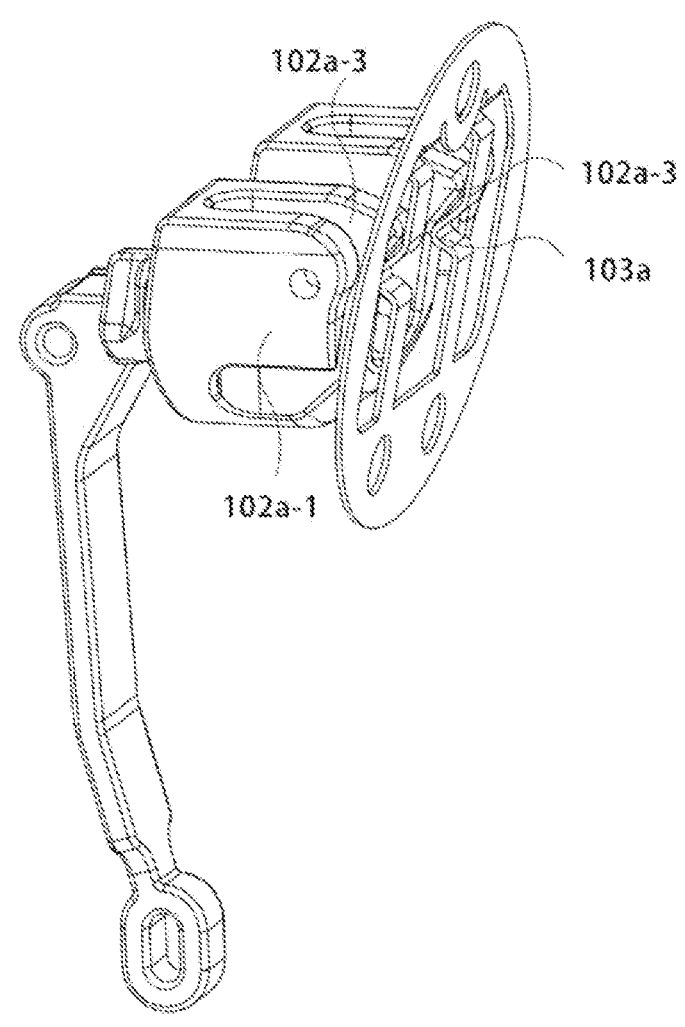
FIG. 4 shows a positional relationship between a toggle lever and the elastic piece of the self-locking device of an endoscope in a non-self-locking state according to the present invention.
Figure 5:
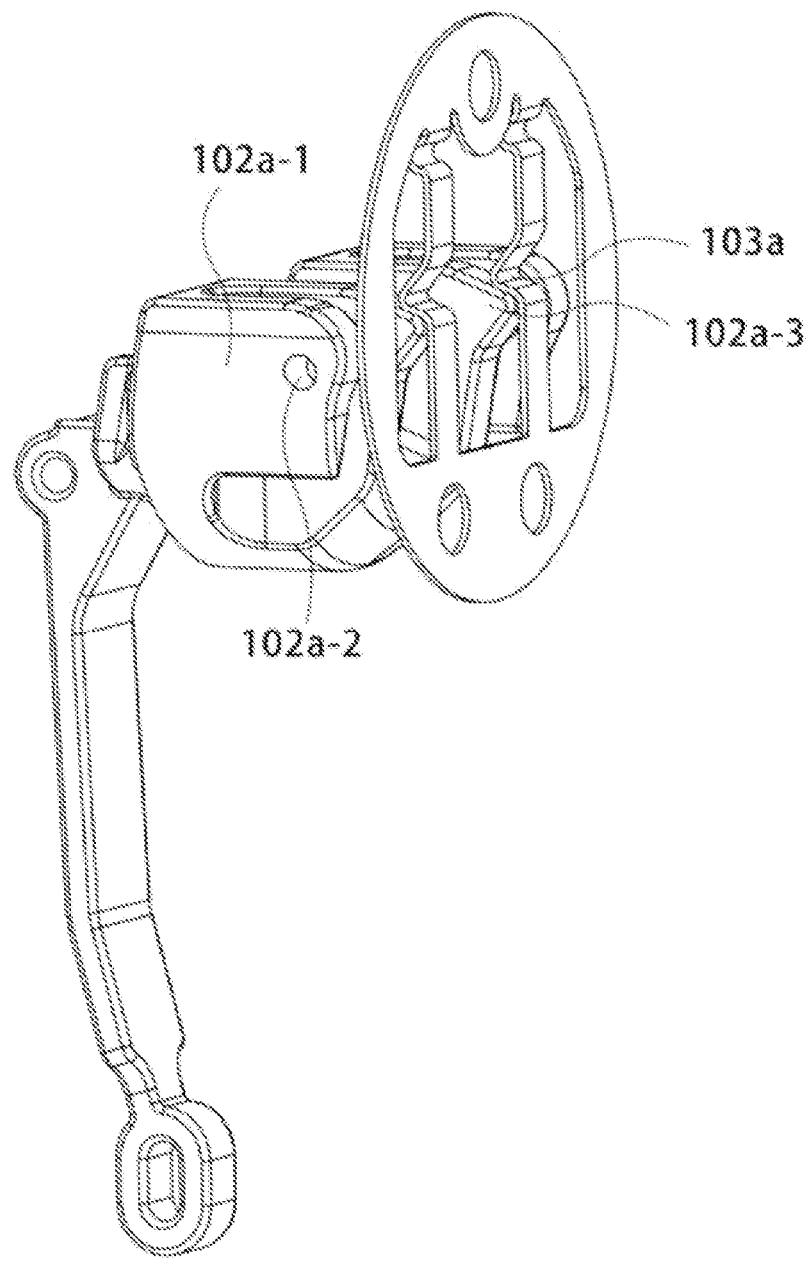
FIG. 5 shows a positional relationship between the toggle lever and the elastic piece of the self-locking device of an endoscope in a self-locking state according to the present invention.
Figure 6:
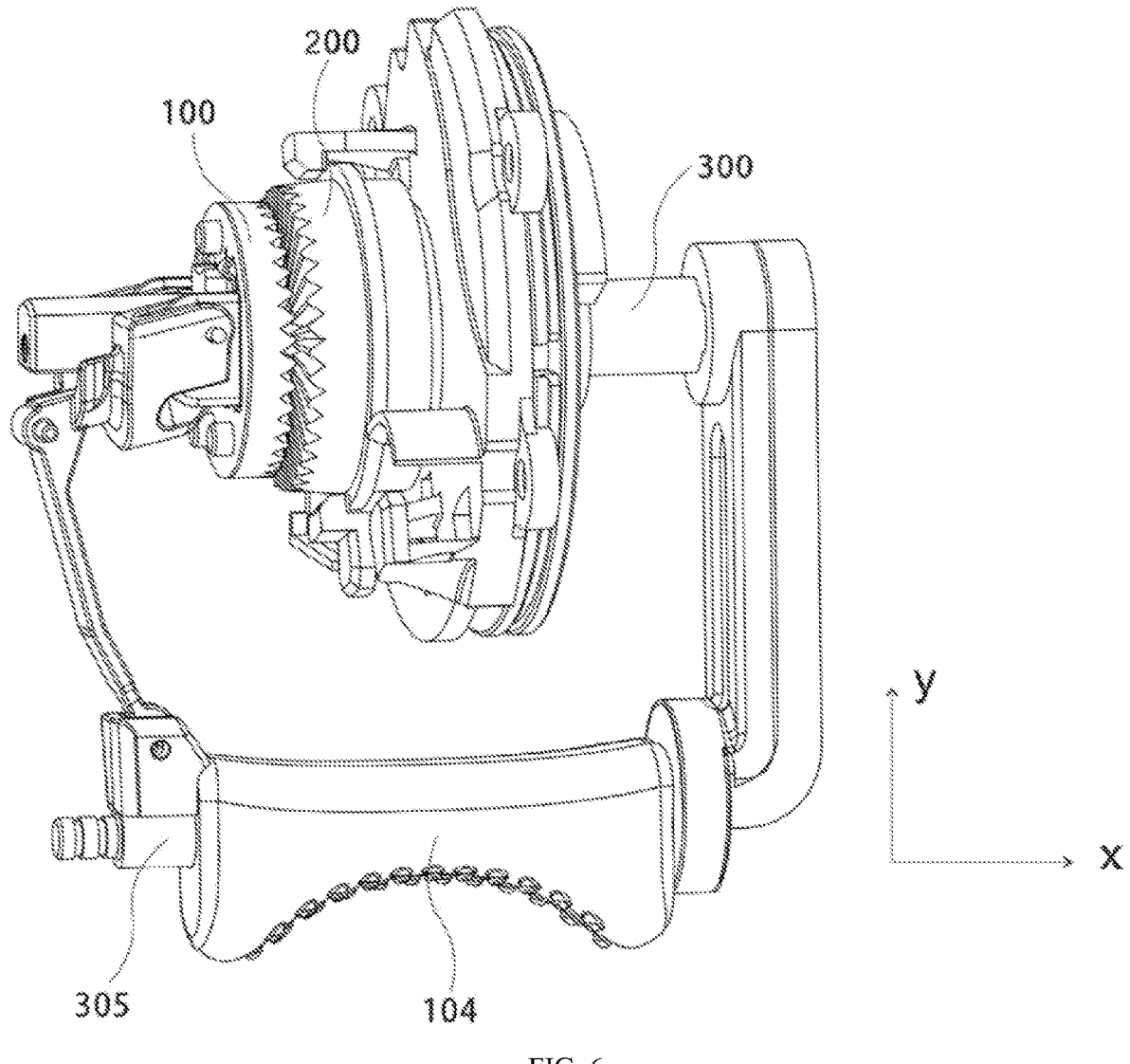
FIG. 6 is a structural view of the self-locking device of an endoscope in a non-self-locking state according to the present invention.
Figure 7:
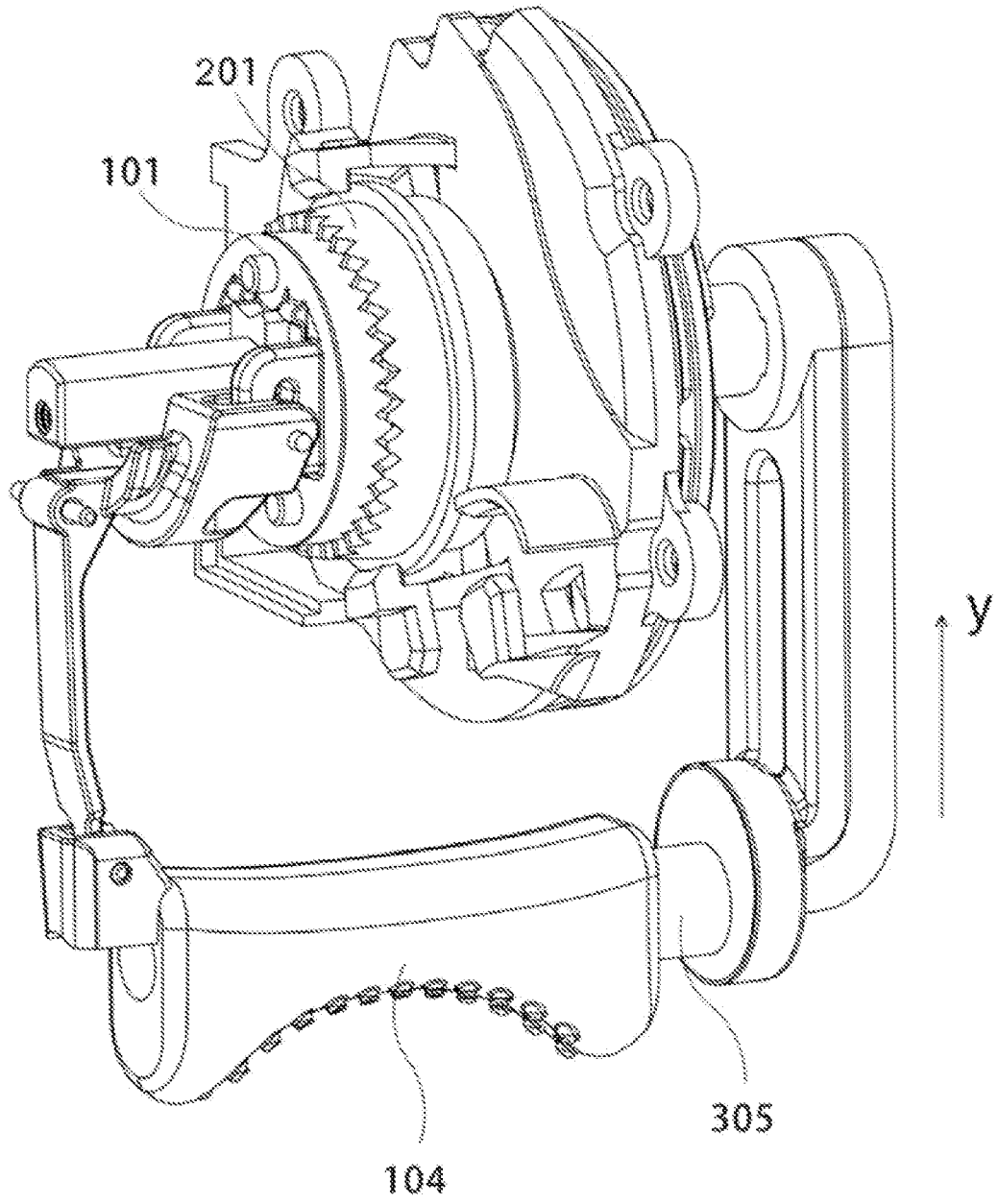
FIG. 7 is a structural view of the self-locking device of an endoscope in a self-locking state according to the present invention.

Referring to FIGS. 1 to 7, the present invention provides a self-locking device of an endoscope. In a first embodiment of the present invention, a main body of the self-locking device includes a connecting assembly 100 and a fitting assembly 200. The connecting assembly 100 and the fitting assembly 200 interact to achieve self-locking and non-self-locking states.

Specifically, the connecting assembly 100 includes a driven gear 101 and a toggle lever 102. The driven gear 101 and the toggle lever 102 are fitted with each other through pins 401. When the toggle lever 102 moves, the driven gear 101 moves left and right relative to the fitting assembly 200, such that the driven gear and the fitting assembly are engaged with each other to form a self-locking state or disengaged from each other to form a non-self-locking state. Here, "left and right" is relative to an orientation shown in the figure. For clarity, in the figure, the positive direction of the x-axis is defined as "right", and "left" or "right" mentioned below will not be explained again.

The fitting assembly 200 includes a driving gear 201. The driving gear 201 is engaged with the driven gear 101 through the toggle lever 102.

It should be noted that the driving gear 201 and the driven gear 101 are gears that are engaged with each other, with respective teeth arranged on opposite surfaces, as shown in the figure.

Preferably, the driven gear 101 includes connecting protrusions 101*a*. The connecting protrusions 101*a* are respectively provided with limiting holes 101*a*-1, and the limiting holes 101*a*-1 are provided with a notch-shaped cross section.

The toggle lever 102 includes a gear connecting block 102*a* and a toggle piece 102*b*. The gear connecting block 102*a* is provided with clamping protrusions 102*a*-1, and recessed areas fitted with the connecting protrusions 101*a* are formed between each two adjacent clamping protrusions 102*a*-1. The clamping protrusions 102*a*-1 are fitted with the connecting protrusions 101*a*, that is, the connecting protrusions 101*a* are respectively inserted between two adjacent clamping protrusions 102*a*-1. The clamping protrusions 102*a*-1 are respectively provided with connecting holes 102*a*-2. The connecting holes 102*a*-2 have a circular cross section, and communicate with the limiting holes 101*a*-1.

Preferably, in order to ensure the stability of the connection, there are four clamping protrusions 102*a*-1 and two connecting protrusions 101*a*, as shown in the figure. However, the number of the clamping protrusions and the connecting protrusions is not limited herein, and other numbers are also within the scope of the present application, and will not be illustrated one by one.

It should be noted that, although the diameter of the limiting holes 101*a*-1 is identical to the diameter of the connecting holes 102*a*-2, the length of the limiting holes 101*a*-1 is greater than the diameter. Therefore, after the pins 401 pass through the limiting holes 101*a*-1 and the connecting holes 102*a*-2 to connect the toggle lever 102 and the driven gear 101, the toggle lever 102 moves up and down along the length of the limiting holes 101*a*-1 along with the pins 401. Here, "up and down" is relative to an orientation shown in the figure. For clarity, in the figure, the positive direction of the y-axis is defined as "up", and "up" or "down" mentioned below will not be explained again.

Embodiment 2

Referring to FIGS. 1 to 7, the present invention provides a self-locking device of an endoscope. Different from the first embodiment, in a second embodiment of the present invention, the self-locking device further includes a fixing assembly 300. The fixing assembly includes a central shaft 301 and a positioning member 302. The driving gear 201 and the driven gear 101 are sequentially sleeved on the central shaft 301. The positioning member 302 is fixed to the central shaft 301 by a bolt. The toggle piece 102b is connected to the positioning member 302 through a pin shaft 402.

Specifically, the connecting assembly 100 includes a driven gear 101 and a toggle lever 102. The driven gear 101 includes connecting protrusions 101a. The connecting protrusions 101a are respectively provided with limiting holes 101a-1, and the limiting holes 101a-1 are provided with a notch-shaped cross section. The toggle lever 102 includes a gear connecting block 102a and a toggle piece 102b. The gear connecting block 102a is provided with clamping protrusions 102a-1, and recessed areas fitted with the connecting protrusions 101a are formed between each two adjacent clamping protrusions 102a-1. The clamping protrusions 102a-1 are fitted with the connecting protrusions 101a. The clamping protrusions 102a-1 are respectively provided with connecting holes 102a-2. The connecting holes 102a-2 have a circular cross section, and communicate with the limiting holes 101a-1. The driven gear 101 and the toggle lever 102 are fitted with each other through pins 401.

Preferably, the gear connecting block 102a and the toggle piece 102b are integrally formed. The gear connecting block 102a is provided with a semi-annular cross section, such that when the gear connecting block 102a moves up and down along the limiting holes 101a-1, interference will not occur. An internal angle between the gear connecting block 102a and the toggle piece 102b is 45-90°, such that the toggle piece 102b can move the gear connecting block 102a, thereby achieving a labor-saving effect.

The fitting assembly 200 includes a driving gear 201. The driving gear 201 is engaged with the driven gear 101 through the toggle lever 102.

The fixing assembly 300 includes a central shaft 301 and a positioning member 302. The driving gear 201 and the driven gear 101 are sequentially sleeved on the central shaft 301. The positioning member 302 is fixed to the central shaft 301 by a bolt. The toggle piece 102b is connected to the positioning member 302 through a pin shaft 402.

Preferably, the pin shaft 402 is hinged to the positioning member 302.

In order to avoid displacement of the driving gear 201, in this embodiment, the fitting assembly 200 further includes a gear fixing member 202. The gear fixing member 202 is fixed to the central shaft 301, and the gear fixing member 202 includes a central protruding block 202a and a rubber ring 202b. The rubber ring 202b is sleeved on an outer contour of the central protruding block 202a, and the driving gear 201 is sleeved on an outer side of the rubber ring 202b. The rubber ring 202b increases the friction between the central protruding block 202a and the driving gear 201.

Preferably, the gear fixing member 202 is provided with a limiting post 202c, and the driving gear 201 is provided with a locking protrusion 201a. The locking protrusion 201a is fitted with the limiting post 202c to limit a position of the driving gear 201.

It should be noted that, in this embodiment, the toggle piece 102b is fixed to the positioning member 302 through the pin shaft 402. Therefore, when an unfixed end of the pick 102b is stressed, the gear connecting block 102a will take the pin shaft 402 as a rotation center, and the other end of the gear connecting block 102a will move through the pins 401 in the limiting holes 101a-1. In this embodiment, in order to adapt to the size and range of motion, the limiting holes 101a-1 are arc-shaped.

When the unfixed end of the toggle piece 102b is pulled, the gear connecting block 102a rotates around the pin shaft 402, and the gear connecting block 102a slides along the limiting holes 101a-1 through the pins 401. When the pins 401 move to a bottom (a bottommost end) of the limiting holes 101a-1, the driving gear 201 and the driven gear 101 are engaged with each other, such that the device completes self-locking. When the pins 401 move to a top (a top end) of the limiting holes 101a-1, the driving gear 201 and the driven gear 101 are disengaged, such that the device releases the self-locking state.

Embodiment 3

Referring to FIGS. 1 to 7, the present invention provides a self-locking device of an endoscope. Different from the second embodiment, in a third embodiment of the present invention, the connecting assembly 100 further includes an elastic piece 103, and the elastic piece 103 is attached to the driven gear 101. The elastic piece 103 is provided with first protrusions 103a. The first protrusions 103a are fitted with pressing protrusions 102a-3 on the gear connecting block 102a.

For ease of understanding, the directions in the figures are taken as an example for detailed description. When the pressing protrusions 102a-3 are below the first protrusions 103a, the device is in a self-locking state. When the pressing protrusions 102a-3 are above the first protrusions 103a, the device is in a non-self-locking state. The mutual cooperation of the pressing protrusions 102a-3 and the first protrusions 103a facilitates the user to determine when the pulling of the gear connecting block 102a is in place by feel.

Preferably, the elastic piece 103 further includes second protrusions 103b. The second protrusions 103b are respectively co-linear with the first protrusions 103a. The second protrusions 103b are used to enhance elastic potential energy on ribs where the first protrusions 103a are located.

Embodiment 4

Referring to FIGS. 1 to 7 the present invention provides a self-locking device of an endoscope. Different from the third embodiment, in a fourth embodiment of the present invention, the connecting assembly 100 further includes a toggle handle 104. One end of the toggle handle 104 is hinged to the toggle piece 102b.

Specifically, the connecting assembly 100 includes a driven gear 101, a toggle lever 102, an elastic piece 103 and a toggle handle 104. The driven gear 101 includes connecting protrusions 101a. The connecting protrusions 101a are respectively provided with limiting holes 101a-1, and the limiting holes 101a-1 are provided with a notch-shaped cross section and are arc-shaped. The toggle lever 102 includes a gear connecting block 102a and a toggle piece 102b. The gear connecting block 102a is provided with clamping protrusions 102a-1, and recessed areas fitted with the connecting protrusions 101a are formed between each two adjacent clamping protrusions 102a-1. The clamping protrusions 102*a*-1 are fitted with the connecting protrusions 101*a*. The clamping protrusions 102*a*-1 are respectively provided with connecting holes 102*a*-2. The connecting holes 102*a*-2 have a circular cross section, and communicate with the limiting holes 101*a*-1. The driven gear 101 and the toggle lever 102 are fitted with each other through pins 401.

Preferably, the gear connecting block 102*a* and the toggle piece 102*b* are integrally formed. The gear connecting block 102*a* is provided with a semi-annular cross section, such that when the gear connecting block 102*a* moves up and down along the limiting holes 101*a*-1, interference will not occur. An internal angle between the gear connecting block 102*a* and the toggle piece 102*b* is 45-90°, such that the toggle piece 102*b* can move the gear connecting block 102*a*, thereby achieving a labor-saving effect.

One end of the toggle handle 104 is hinged to the toggle piece 102*b*.

The elastic piece 103 is attached to the driven gear 101. The elastic piece 103 is provided with first protrusions 103*a*. The first protrusions 103*a* are fitted with pressing protrusions 102*a*-3 on the gear connecting block 102*a*.

The fitting assembly 200 includes a driving gear 201 and a gear fixing member 202. The driving gear 201 is engaged with the driven gear 101 through the toggle lever 102. The gear fixing member 202 is fixed to the central shaft 301, and the gear fixing member 202 includes a central protruding block 202*a* and a rubber ring 202*b*. The rubber ring 202*b* is sleeved on an outer contour of the central protruding block 202*a*, and the driving gear 201 is sleeved on an outer side of the rubber ring 202*b*.

The fixing assembly 300 includes a central shaft 301 and a positioning member 302. The driving gear 201 and the driven gear 101 are sequentially sleeved on the central shaft 301. The positioning member 302 is fixed to the central shaft 301 by a bolt. The toggle piece 102*b* is connected to the positioning member 302 through a pin shaft 402.

Preferably, the pin shaft 402 is hinged to the positioning member 302.

Preferably, the fixing assembly 300 further includes a handle limiting member 304 and a connecting shaft 305. The handle limiting member 304 is fixed to the other side of the central shaft 301. The connecting shaft 305 passes through the toggle handle 104, and is connected to the handle limiting member 304.

Preferably, the gear fixing member 202 is provided with a limiting post 202*c*, and the driving gear 201 is provided with a locking protrusion 201*a*. The locking protrusion 201*a* is fitted with the limiting post 202*c* to limit a position of the driving gear 201.

The toggle handle 104 is slid such that the toggle handle 104 moves to a leftmost side. When the pins 401 move to a bottom (a bottommost end) of the limiting holes 101*a*-1, the driving gear 201 and the driven gear 101 are engaged with each other, such that the device completes self-locking. The toggle handle 104 is slid such that the toggle handle 104 moves to a rightmost side. When the pins 401 move to a top (a top end) of the limiting holes 101*a*-1, the driving gear 201 and the driven gear 101 are disengaged, such that the device releases the self-locking state. Through the design of a lever structure, the self-locking device switches the driven gear and the driving gear between engaged and disengaged states without resorting to an external force of a part, which avoids the use of the part and extends the service life of the device.

It should be noted that the above embodiments are only intended to explain, rather than to limit the technical solutions of the present invention. Although the present invention is described in detail with reference to the preferred embodiments, those skilled in the art should understand that modifications or equivalent substitutions may be made to the technical solutions of the present invention without departing from the spirit and scope of the technical solutions of the present invention, and such modifications or equivalent substitutions should be included within the scope of the claims of the present invention.

What is claimed is:

1. A self-locking device of an endoscope, comprising:
   a connecting assembly, comprising a driven gear and a toggle lever, wherein the driven gear and the toggle lever are fitted with each other through pins; and
a fitting assembly, comprising a driving gear, wherein the driving gear is engaged with the driven gear through the toggle lever;
   wherein the driven gear comprises limiting holes having an arc-shaped cross section, and the toggle lever comprises a gear connecting block provided with connecting holes,
   wherein the pins pass through the arc-shaped limiting holes and the connecting holes and are configured to enable the toggle lever to rotate along a curved path defined by the arc-shaped limiting holes as the toggle lever transitions the driving gear and the driven gear between a self-locking state and a non-self-locking state.

2. The self-locking device of the endoscope according to claim 1, wherein
   the toggle lever comprises a gear connecting block and a toggle piece, wherein the gear connecting block and the toggle piece are integrally formed; and
   the gear connecting block is provided with a semi-annular cross section, and an internal angle between the gear connecting block and the toggle piece is 45-90°.

3. The self-locking device of the endoscope according to claim 2, wherein
   the driven gear comprises connecting protrusions, wherein the connecting protrusions are respectively provided with the limiting holes;
   the gear connecting block is provided with clamping protrusions, the clamping protrusions are respectively provided with the connecting holes,
   and the limiting holes have a diameter identical to a diameter of the connecting holes and a length greater than the diameter.

4. The self-locking device of the endoscope according to claim 3, further comprising:
   a fixing assembly, comprising a central shaft and a positioning member, wherein the positioning member is fixed to the central shaft by a bolt;
   wherein the driving gear and the driven gear are sequentially sleeved on the central shaft; and
   the toggle piece is connected to the positioning member through a pin shaft.

5. The self-locking device of the endoscope according to claim 4, wherein
   the fitting assembly further comprises a gear fixing member;
   the gear fixing member is fixed to a first side of the central shaft, and the gear fixing member comprises a central protruding block and a rubber ring;
   the rubber ring is sleeved on an outer contour of the central protruding block; and
   the driving gear is sleeved on an outer side of the rubber ring.

6. The self-locking device of the endoscope according to claim 5, wherein the connecting assembly further comprises a toggle handle, wherein one end of the toggle handle is hinged to the toggle piece.

7. The self-locking device of the endoscope according to claim 6, wherein the connecting assembly further comprises an elastic piece, wherein the elastic piece is attached to the driven gear;

the elastic piece is provided with first protrusions; and the first protrusions are fitted with surfaces of the clamping protrusions of the gear connecting block, wherein the surfaces of the clamping protrusions of the gear connecting block abut against the elastic piece.

8. The self-locking device of the endoscope according to claim 7, wherein the elastic piece further comprises second protrusions, wherein the second protrusions are respectively co-linear with the first protrusions.

9. The self-locking device of the endoscope according to claim 4, wherein the fixing assembly further comprises a handle limiting member, wherein the handle limiting member is fixed to a second side of the central shaft.

10. The self-locking device of the endoscope according to claim 9, wherein the fixing assembly further comprises a connecting shaft, wherein the connecting shaft passes through the toggle handle, and the connecting shaft is connected to the handle limiting member.

11. The self-locking device of the endoscope according to claim 5, wherein the fixing assembly further comprises a handle limiting member, wherein the handle limiting member is fixed to a second side of the central shaft.

12. The self-locking device of the endoscope according to claim 6, wherein the fixing assembly further comprises a handle limiting member, wherein the handle limiting member is fixed to a second side of the central shaft.

13. The self-locking device of the endoscope according to claim 7, wherein the fixing assembly further comprises a handle limiting member, wherein the handle limiting member is fixed to a second side of the central shaft.

14. The self-locking device of the endoscope according to claim 8, wherein the fixing assembly further comprises a handle limiting member, wherein the handle limiting member is fixed to a second side of the central shaft.

* * * * *